United States Patent

Hardtmann

[11] 3,959,483
[45] May 25, 1976

[54] PHENOXY-4-ISOCYANO-BUTAN-2-OLS

[75] Inventor: Goetz E. Hardtmann, Morristown, N.J.

[73] Assignee: Sandoz, Inc., E. Hanover, N.J.

[22] Filed: Aug. 22, 1975

[21] Appl. No.: 606,930

[52] U.S. Cl. .............................. 424/304; 260/465 F
[51] Int. Cl.² ............... A61K 31/275; C07C 121/75
[58] Field of Search .................. 260/465 F; 424/304

[56] References Cited
UNITED STATES PATENTS 3,855,249  12/1974  Lafon ............................. 260/465 X

*Primary Examiner*—Lewis Gotts
*Assistant Examiner*—Dolph H. Torrence
*Attorney, Agent, or Firm*—Gerald D. Sharkin; Richard E. Vila

[57] ABSTRACT

Sedative/hypnotics of the formula

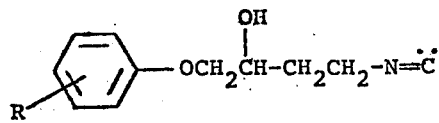

wherein R is hydrogen, halo, alkyl, alkoxy or trifluoromethyl, are prepared by reacting a phenyl-2,3-epoxypropyl ether with methyl isocyanide.

10 Claims, No Drawings

PHENOXY-4-ISOCYANO-BUTAN-2-OLS

The present invention relates to phenoxy-4-isocyano-butan-2-ols, their preparation and pharmaceutical methods and compositions for utilizing the pharmacological properties of such compounds, particularly as CNS depressant agents having activity as sedative/hypnotics.

The compounds of the present invention may be represented by the following structural formula I:

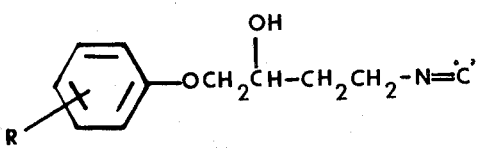

wherein R is hydrogen, halo of atomic weight of from 18 to 80, i.e., fluoro, chloro or bromo, alkyl of 1 to 6 carbon atoms, alkoxy of 1 to 6 carbon atoms or trifluoromethyl.

The compounds of the formula I may be prepared by reacting a compound of the formula II:

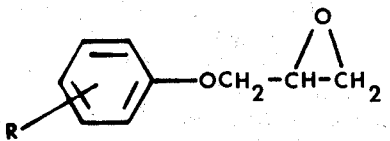

wherein R is as above defined, with a compound of the formula III:

wherein $M^+$ is the cation derived from a proton abstracting agent.

The preparation of Compounds I may be carried out at temperatures in the range of from minus 120°C. to 0°C., preferably minus 80°C. to minus 10°C., in an inert organic solvent, and under essentially anhydrous conditions. The particularly suitable organic solvents are of the aprotic type and the preferred solvents include the ethers such as tetrahydrofuran. The reaction is exothermic and controlled accordingly, and the resulting product of the formula I may be recovered from the reaction mixture in which it is formed by working up by established procedures.

The compound of the formula III is prepared in situ by reacting the compound of the formula IIIA

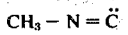

with a proton abstracting agent in an organic solvent which is of the type suitable for the reaction of compounds II and III. Reaction temperatures may be generally of the order of from minus 150°C. to 0°C., preferably minus 120°C. to minus 40°C. The proton abstracting agents are those which will dislodge a hydrogen atom from the methyl group of compound IIIA to result in the ionic product III. Such agents are of well known types and are represented by the stronger bases. The generally preferred agents are the butyl lithiums such as n-butyl lithium and t-butyl lithium, in which case M is lithium and a by-product butane is formed. Other such agents which may be mentioned include the alkali metal hydrides such as sodium hydride. In general, M is an alkali metal. The mol ratio of the proton abstracting agent to the compound IIIA is not particularly critical but is preferably in the range of 0.8:1 to 1.5:1, desirably about 1:1. While the preparation of the compound III may be carried out in the presence of the compound II and/or the reaction leading to compounds I, it is generally preferred to substantially complete the preparation of the compound III prior to combining with the compound II.

The compound IIIA is known and the compounds of the formula II are also known or may be prepared from known materials by procedures established for the known compounds II.

The compound of the formula I are useful as sedative/hypnotics as indicated by a reinduction of hexobarbital anesthesia in mice (10-200 mg./kg.) and by a potentiation of Thioridazine as determined by a loss of righting reflex according to the method of Reed-Muench, Am. J. Hygiene, 27: 493–497 (1937), in which fasted but glucose maintained mice are administered 12.5 mg./kg. i.p. of Thioridazine followed immediately by the administration of graded doses totally from 10 to 150 mg./kg., i.p. of the test compound in a volume 0.1 ml./kg., of body weight, the mice being scored for loss of righting reflex sixty minutes after dosing.

The sedating effective dosage of the compounds of the formula I will also vary depending upon known factors. However, in general, satisfactory results are obtained when the compounds are administered in a single dose at bedtime of from 2 to 200 milligrams per kilogram of body weight. For most mammals, the administration of a single dose of from 140 to 1500 milligrams provides satisfactory results and is typically administered at bedtime in admixture with a solid or liquid pharmaceutical carrier.

For the above usages, the compounds of the formula I are preferably combined with one or more conventional pharmaceutically acceptable carriers, and such other conventional adjuvants as may be desired or necessary, and the resulting composition administered orally in such forms as tablets, capsules, granules, dispersible powders, elixirs, syrups, suspensions and the like parenterally in the form of an injectable solution, suspension or the like, e.g., a sterile injectable aqueous suspension. Such compositions may be prepared according to any method known in the art for the manufacture of pharmaceutical compositions. In general, the compositions of the invention adapted for either oral or parenteral administration may contain 1% to 90% by weight of the active ingredient in combination with the inert carrier, more usually 10% to 70%.

The preferred mode of administration is oral administration and preferred pharmaceutical compositions from the standpoint of preparation and ease of administration are solid compositions, particularly hardfilled capsules and tablets.

A representative formulation for administration at bedtime for sedating a mammal is a capsule prepared by standard techniques to contain the following:

| Ingredient | Weight (mg.) |
|---|---|
| 1-p-tert. butylphenoxy-4-isocyano-butan-2-ol | 150 |
| Kaolin | 150 |

The following examples illustrate compounds of the invention and their preparation.

EXAMPLE 1

1-p-tert. butylphenoxy-4-isocyano-butan-2-ol

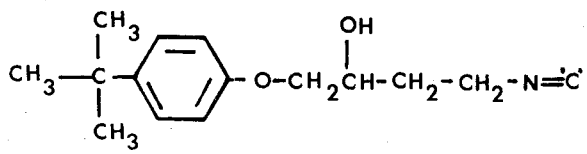

To a solution prepared by combining 28 ml. of 0.1 g./ml. solution of n-butyl lithium in hexane with 50 ml. of tetrahydrofuran there is added dropwise at the temperature of a dry ice/actone bath a solution of 2.8 ml. of methyl isocyanide in 10 ml. of tetrahydrofuran followed by stirring for 10 minutes. There is then added dropwise 8.0 g. of p-tert. butylphenyl-2,3-epoxypropyl ether in 30 ml. of tetrahydrofuran and the temperature is allowed to rise to minus 20°C. The resulting solution is then stirred for an additional 30 minutes at minus 20°C. to minus 25°C. The reaction mixture is then cooled to minus 50°C., water added dropwise, the tetrahydrofuran stripped off in vacuo, the residue extracted twice with ethyl acetate and the combined extracts washed once with water, treated with charcoal and evaporated in vacuo to dryness. The residue is taken up in ether which is exchanged for petroleum ether/pentane (1:1) on a steam bath to obtain 1-p-tert. butylphenoxy-4-isocyano-butan-2-ol, m.p. 69°-72°C.

EXAMPLE 2

Following the procedure of Example 1, the following compounds of the invention are prepared:
A. 1-p-methylphenoxy-4-isocyano-butan-2-ol.
B. 1-p-methoxyphenoxy-4-isocyano-butan-2-ol.
C. 1-p-chlorophenoxy-4-isocyano-butan-2-ol.
D. 1-m-trifluoromethylphenoxy-4-isocyanobutan-2-ol.
E. 1-phenoxy-4-isocyano-butan-2-ol.

What is claimed is:

1. A compound of the formula:

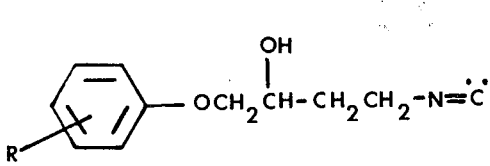

wherein R is hydrogen, fluoro, chloro, bromo, alkyl of 1 to 6 carbon atoms, alkoxy of 1 to 6 carbon atoms or trifluoromethyl.

2. A compound of claim 1 in which R is at the para position of the phenyl ring to which it is attached.

3. A compound of claim 2 in which R is branched alkyl of 3 to 6 carbon atoms.

4. The compound of claim 3 which is 1-p-tert. butylphenoxy-4-isocyano-butan-2-ol.

5. The compound of claim 2 which is 1-p-chlorophenoxy-4-isocyano-butan-2-ol.

6. The compound of claim 2 which is 1-p-methoxyphenoxy-4-isocyano-butan-2-ol.

7. The compound of claim 1 which is 1-m-trifluoromethylphenoxy-4-isocyano-butan-2-ol.

8. The compound of claim 1 which is 1-phenoxy-4-isocyano-butan-2-ol.

9. The method of sedating a mammal comprising administering a sedating effective amount of compound of claim 1.

10. A pharmaceutical composition comprising an inert pharmaceutically acceptable carrier and a sedating effective amount of a compound of claim 1.